United States Patent

Winter

[11] 4,077,251
[45] Mar. 7, 1978

[54] VISCOSITY MEASURING DEVICE AND METHOD

[76] Inventor: Horst H. Winter, Sommerhaldenweg 90, Stuttgart, Germany

[21] Appl. No.: 759,156

[22] Filed: Jan. 13, 1977

[30] Foreign Application Priority Data

Jan. 16, 1976 Germany ............... 2601487

[51] Int. Cl.² .................................. G01N 11/14
[52] U.S. Cl. ........................................ 73/59
[58] Field of Search ................................ 73/59, 60

[56] References Cited

U.S. PATENT DOCUMENTS 3,885,418  5/1975  Kriebel ........................... 73/59

FOREIGN PATENT DOCUMENTS 1,294,950  4/1962  France ............................. 73/59
1,254,887  8/1962  Germany ......................... 73/59

Primary Examiner—Richard C. Queisser
Assistant Examiner—Joseph W. Roskos
Attorney, Agent, or Firm—Fred Philpitt

[57] ABSTRACT

A rotary viscosimeter of a modified Couette-type for continuous measurements of the viscosity of non-Newtonian fluids. The fluid to be tested is shorn in an annular gap between concentric cylinders in circumferential direction. In order to bring about an axial flow through the annulus, the geometry of one of the cylinders is modified such that a small axial pressure gradient is formed. The modification consists of small grooves while the main part of the cylinder surface remains unchanged. The torque in the system is substantially determined by the viscometric flow in the circumferential direction and not by the rotational flow in the grooves.

5 Claims, 6 Drawing Figures

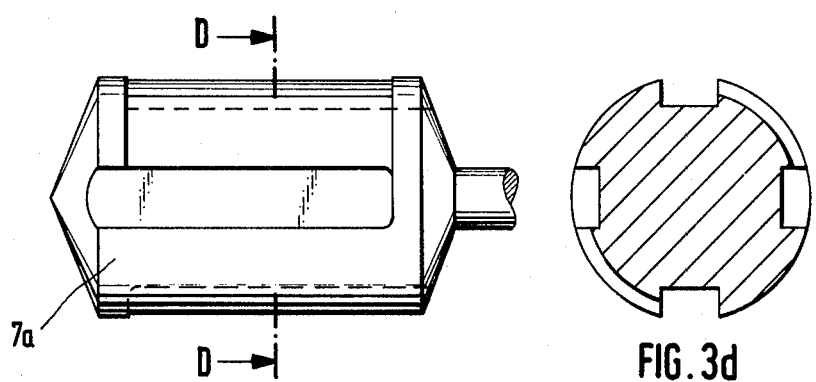
FIG. 3a
FIG. 3d
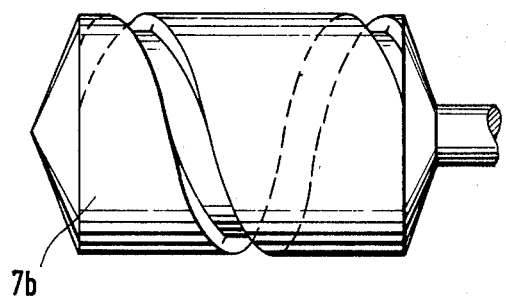
FIG. 3b
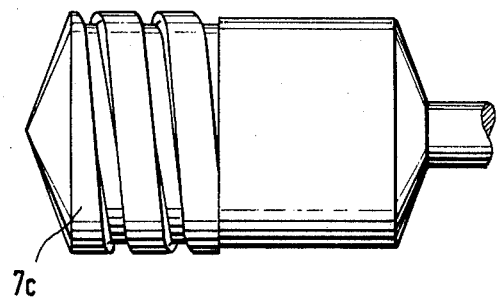
FIG. 3c

VISCOSITY MEASURING DEVICE AND METHOD

The viscosity $\eta$ is defined as the quotient of the shear stress $\tau$ and the shearing speed $\gamma$:

$$\eta = \tau/\gamma \ [\text{N s/m}^2].$$

In Newtonian fluids the viscosity is a function of pressure and temperature, while in non-Newtonian fluids the viscosity depends additionally on the shearing speed.

In order to record the flow lines $\gamma = f(\tau)$ and $\tau = f(\gamma)$ respectively, which form the basis of the rheological data calculation, the following three basic types of rheometers are usually used for thermoplastic materials:

1. Capillary rheometers having a bore or slot;
2. Rotational rheometers having a cylindrical shearing gap
   a. for an operation involving enclosed substances or
   b. for an operation involving flowing substances;
3. Rotational rheometers having a plane-parallel or wedge-shaped shearing gap for an operation involving enclosed substances.

Group (1) is preferably eligible for highly viscous polymeric molten materials, while groups (2) and (3) are more frequently used for fluids having a low viscosity, such as polymer solutions.

The viscosimeter described hereinafter falls under group (2b). The test material passes through the viscosimeter. Superimposed on the drag flow is a pressure flow, which usually has a procedurally predetermined pressure differential $\Delta p$ (H. K. Bruss, Kunststoffe 60, 162 - 164 (1970) or is produced by a separate pumping unit. Such a pumping unit may be for example, a gear pump or a screw extruder (German Offenlegungsschrift No. 1798201). Owing to its geometry, (in most cases, it is a plain cylinder), the rotor of the rheometer cannot deliver the material through the measuring gap. The rotor is driven independently of the pump drive, or if the rotor and the delivery unit are coaxially connected together and are jointly driven, the viscosity is determined from the torque measured for the rotor of the viscosimeter (German Offenlegungsschrift No. 1798201).

In an operation involving flowing substances, dissipated heat is delivered convectively from the measuring gap, and it is possible to carry out viscosity measurements even at relatively high shearing speeds. Another reason for operating a rheometer as a flow unit emerges when the viscosity is monitored over a longer period. To this end, there are continuously taken from a process samples whose viscosity is determined by means of a rheometer. The delay periods between the taking of samples and the viscosity measurement are shortest when the rheometer is operated directly by the flow method.

The task underlying the invention is to find a rotational rheometer for flowing substances which operates independently of a pump or an externally predetermined pressure differential. The rotational rheometer therefore has to provide an unaided delivery. The method should provide metrological statements about the viscosity of Newtonian or non-Newtonian substances. The task includes furthermore the determination of rheological data (viscosity) in order to characterise qualitative changes in the test materials, particularly changes in concentration in regard to time and homogenising effects in the preparation and processing of the respective substances.

The method according to the invention is characterised in that the substance to be tested is deformed simultaneously in several shear fields, but at least in one drag flow field and one pressure flow field, within a system which is set up for a continuous throughput of substances. The mass flow is kept in motion by a rotor (or housing) effecting the delivery. The external pressure differential $\Delta p$ between the ends of the rotor should equal zero, if possible; however, $\Delta p$ may also have positive or negative values. The torque and the operating speed on the rotor (or the housing) is measured or pre-set.

The device according to the invention is characterised by a functional element which is rotatably arranged in a housing, preferably a hollow cylinder, and which is called hereinafter "rotor" and which forms, together with the inside wall of the housing, a shearing gap. The system is provided with at least one inlet and one outlet, allowing the material to be tested to flow continuously through the system.

Figure 1:
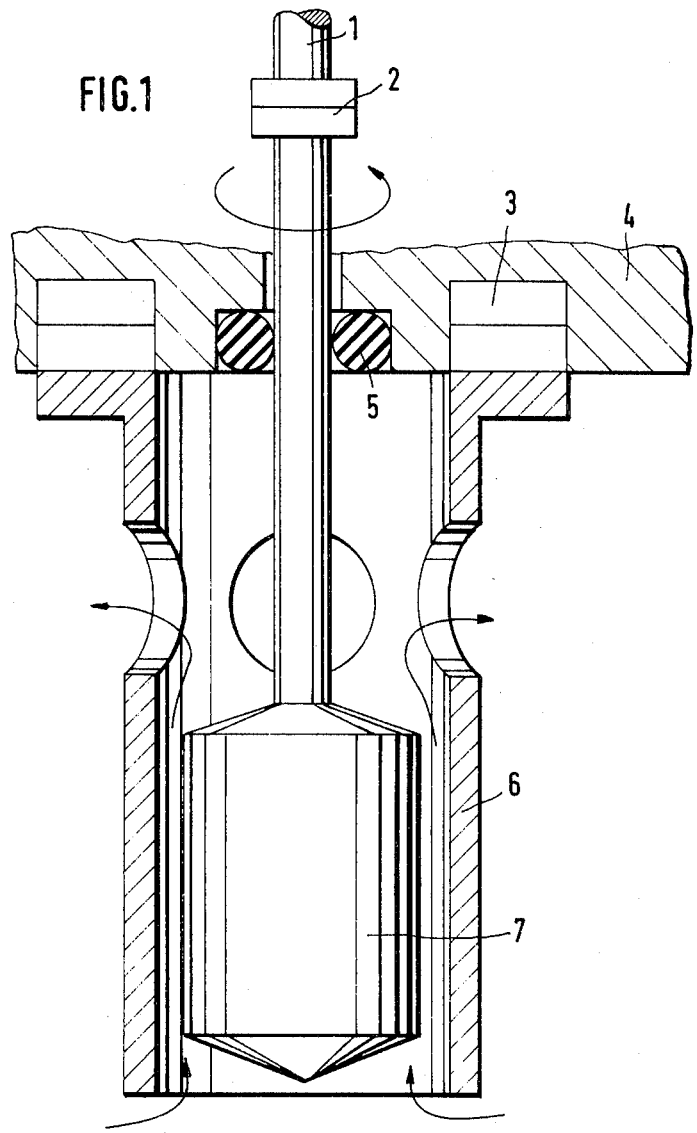
FIG. 1 is a partly sectional view of a first embodiment of the invention with details of the rotor profile omitted.
Figure 2:
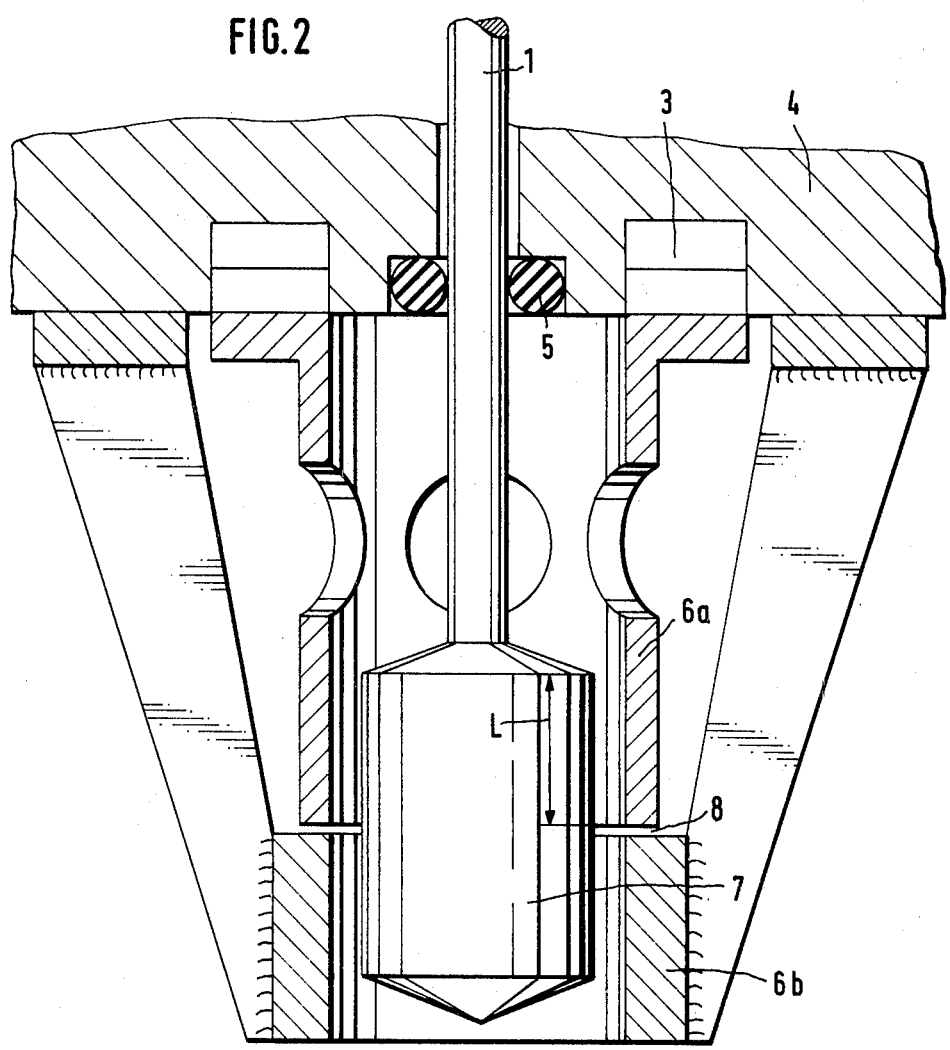
FIG. 2 is a view similar to FIG. 1 showing a second embodiment of the invention.

FIGS. 3(a) through 3(c) are isometric views of the three different embodiments of a rotor for use in the devices of FIG. 1 and FIG. 2; and FIG. 3(d) is cross section of the rotor shown in FIG. 3(a) along the line D — D in FIG. 3(a).

FIG. 1 shows a diagram of my device. The rotor 7 is located in a housing 6. The rotor is driven through the shaft 1 at a pre-set rotational speed or by a rotational speed programme. The torque is measured on the shaft (sensor 2) or on the housing (sensor 3). The space, which is filled with the test fluid, is sealed towards the drive by the seal 5.

When the torque is measured on the housing, the gap can be split between the rotor and housing, as for example shown in FIG. 2. The torque is measured only for a portion of the rotor (measuring gap of the length L). The other portion of the rotor runs in a housing part 6b, which is fixedly connected to the base plate 4 via holders. The gap 8 between the housing part 6a and the housing part 6b may be sealed by a flexible seal, but this is not compulsory. The measuring gap may be chosen on the upper part of the rotor (design shown in FIG. 2) or on the lower part of the rotor.

On a rotational rheometer of group (2b), such as is usually employed for viscosity measurements, the rotor is a plain cylinder which forms, together with the plain inside cylinder of the housing, an annular gap. During the rotation of the inside (or the outside) cylinder, the substance to be tested is shorn in the circumferential direction. In order to bring about additionally an axial flow through the flow gap, the geometry of the rotor and/or the geometry of the housing of the viscosimeter described here is modified so that a small axial pressure gradient is formed. Some examples of such geometries are given in illustration 3. The rotors shown provide, together with a plain external cylinder, a system of efficient delivery. Alternatively, delivery efficient geometries could be selected for the housing and be operated together with a profiled or plain rotor.

The first of the exemplified embodiments shown in illustration 3 is a so-called "blind-groove torpedo" 7a. The pressure at the inlet and outlet of the system being equal ($\Delta p = 0$), the delivered volume flow can be calculated (G. Schenkel, Industrie-Anzeiger 94, 2092 – 2096 (1972). On the rotor 7b, there is cut into the cylindrical portion a helical duct which ensures the axial transportation as in the known system screw/cylinder. The rotor 7c is split into the delivery zone (screw) and the shearing zone (plain cylinder). In all the three examples, the energy for the axial delivery process as well as the energy for the shear in the circumferential direction is introduced into the mass to be tested by the torque on the shaft. The design which is most favourable viscosimetrically for a specific material is that where the torque is substantially determined by the shear in the circumferential direction.

I claim:

1. In the known device for determining the viscosity of fluids which includes a housing and a rotor mounted coaxially within said housing so that an annular shearing gap is left between the exterior surface of said rotor and the interior surface of said housing, the improvement which comprises providing narrow and shallow grooves in at least one of said surfaces, the dimensions of said grooves being small as compared to the total surfaces so that a small axial flow of the fluid to be tested is effected by said grooves while the fluid flow pattern in a circumferential direction is left essentially unchanged.

2. A device according to claim 1 wherein said rotor surface is provided with an axially extenting blind-groove torpedo.

3. A device according to claim 1 wherein said rotor surface is provided with a screw channel.

4. A device according to claim 1 wherein said rotor is connected to means for measuring torque.

5. A device according to claim 1 wherein said housing is connected to means for measuring torque.

* * * * *